United States Patent [19]
Kjerstad

[11] Patent Number: 5,167,244
[45] Date of Patent: Dec. 1, 1992

[54] TOBACCO SUBSTITUTE

[76] Inventor: Randy E. Kjerstad, 708 8th St., Apt. 2, Brookings, S. Dak. 57006

[21] Appl. No.: 467,578

[22] Filed: Jan. 19, 1990

[51] Int. Cl.$^5$ .............................. A24D 47/00
[52] U.S. Cl. .................... 131/359; 131/352
[58] Field of Search ............ 131/359, 369, 352

[56] References Cited

U.S. PATENT DOCUMENTS

| | | |
|---|---|---|
| 2,930,720 | 3/1960 | Finberg . |
| 3,067,068 | 12/1962 | Finberg . |
| 3,071,476 | 1/1963 | Werft et al. . |
| 3,369,551 | 2/1968 | Carroll . |
| 3,757,798 | 9/1973 | Lambert . |
| 4,431,680 | 2/1984 | Yoshida . |

Primary Examiner—V. Millin
Attorney, Agent, or Firm—Bill D. McCarthy; Glen M. Burdick

[57] ABSTRACT

A tobacco substitute is provided wherein granulated cellulose wetted with a casing solution is sealingly enveloped in a saliva permeable infusion pouch. The filled infusion pouch is sized so that the filled infusion pouch can be placed in a person's mouth in an area adjacent an outer gum to assist in reducing the person's dependency on tobacco. The casing solution, which is present in amount of up to about 30 weight percent, provides the tobacco substitute with taste and aroma properties which satisfy the desires of the user. The casing solution consists essentially of about 63 to 82 weight percent water, from about 1 to 5 weight percent of a flavoring agent, from about 15 to about 25 weight percent sweetener and from about 2 to about 7 weight percent of a humectant. A method for producing the improved tobacco substitute is also disclosed, as is a method for reducing dependency on tobacco using such tobacco substitute.

17 Claims, 1 Drawing Sheet

TOBACCO SUBSTITUTE

BACKGROUND OF THE INVENTION

1. Field of the Invention

The present invention relates to a tobacco substitute, and more particularly, but not by way of limitation, to a saliva permeable infusion pouch enveloping and sealingly retaining a tobaccoless composition which may be used in lieu of tobacco.

2. Discussion

Evidence is mounting as to the health hazards associated with the use of tobacco in any form, whether smoking or non-smoking usage. Because of such evidence, more effort has been exerted to find smoking and chewing substitutes, including the utilization of leafy plants to either completely replace tobacco or to reduce the tobacco content of various tobacco products.

Carroll, U.S. Pat. No. 3,369,551 discloses a tobacco substitute made from leafy plants, such as lettuce, cabbage, broccoli, collard, kohlrabi, spinach and papaya. In producing the tobacco substitute the leafy material is stripped of substantially all of its ingredients except carbohydrates and nitrogen compounds, such as proteins, and appropriate flavoring ingredients are added to the stripped leafy material in order to impart taste and aroma to the product commensurate with that of a tobacco product. The stripping of the leafy material in producing the tobacco substitute is effected in two phases, the first phase being a water extraction phase wherein the water insoluble ingredients of the leafy material are extracted, the second phase being an organic solvent extraction phase wherein pigments, chlorophyll, carotene, xanthophyll and similar products are extracted.

Lambert, U.S. Pat. No. 3,757,798 discloses a method for reducing dependency on cigarette smoking or tobacco usage wherein a series of infusion bags containing tobacco in decreasing amounts are sequentially placed in a person's mouth so that the solution or juice of the tobacco contained within the bag passes therethrough for ingestion by the mouth tissues and the digestive system of the user.

Finberg, U.S. Pat. No. 3,067,068 discloses a tobacco-like composition consisting of papaya leaves and a casing material which contains little or no nicotine. The tobacco-like composition can be used as plugs or wads for chewing. Finberg, U.S. Pat. No. 2,930,720 also discloses the use of papaya leaves in formulating a smoking composition.

While numerous attempts have been made to reduce the nicotine content of tobacco products, as well as to produce commercially acceptable nicotine-free tobacco-like compositions which can be utilized as a substitute for tobacco, new and improved tobacco free compositions are constantly being sought which will assist the person physiologically or psychologically addicted to tobacco to more easily cease from the use of tobacco. It is to such a tobacco free composition that the present invention is directed.

SUMMARY OF THE INVENTION

According to the present invention a tobacco substitute is provided wherein granulated cellulose wetted with a casing solution is sealingly enveloped in a saliva permeable infusion pouch. The filled infusion pouch is sized so that the filled infusion pouch can be placed in a person's mouth in an area adjacent an outer gum to assist in reducing the person's dependency on tobacco. The casing solution, which is employed in an amount of up to about 30 weight percent, based upon the weight of the granulated cellulose, provides the tobacco substitute with taste and aroma properties which satisfy the desires of the user. The casing solution, which is employed to wet the granulated cellulose (and thereby provide the desired moisture to the granulated cellulose) consisting essentially of from about 63 to about 82 weight percent water, from about 1 to about 5 weight percent of a flavoring agent, from about 15 to about 25 weight percent sweetener and from about 2 to about 7 weight percent of a humectant.

In another aspect the present invention provides a method for producing an improved chewing tobacco substitute wherein the tobacco substitute is disposed in a saliva permeable infusion pouch sized to be positioned in a person's mouth adjacent the outer gum and inner cheek so that the flavor of the tobacco substitute, which is a tobaccoless composition, can be used to satisfy the user's desire for tobacco.

An object of the present invention is to provide an improved tobacco substitute which can be utilized to reduce a person's dependency on tobacco.

Another object of the present invention, while achieving the before stated object, is to provide a tobacco free composition which is convenient and sanitary to use, and yet is readily disposable once depleted by the user.

Another object of the present invention while achieving the before-stated objects, is to provide a nicotine-free tobacco free composition which has a taste, color, texture, aroma and flavor quality resembling that of commercially available snuff and other tobacco products.

Other objects, advantages and features of the present invention will be apparent from the following description when read in conjunction with the drawings and appended claims.

DESCRIPTION

Figure 1:
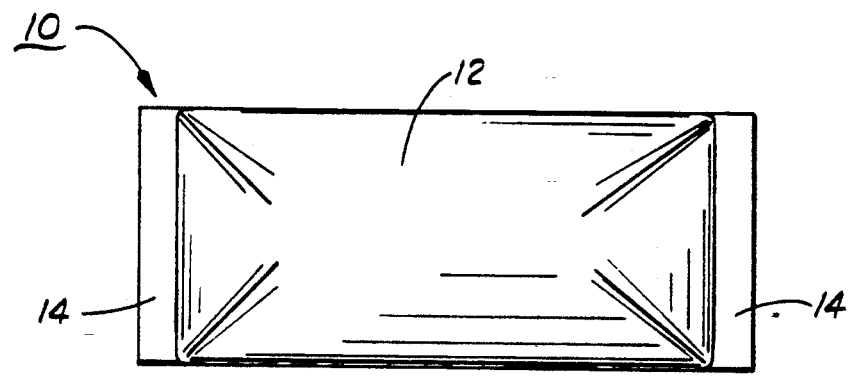
FIG. 1 is a front view of saliva permeable infusion pouch in accordance with the present invention.

The present invention provides an unique tobacco substitute which can be employed to reduce a person's dependency on tobacco, and thus the craving for nicotine. Further, the tobacco substitute, while possessing desirable features similar to those of commercially acceptable tobacco snuff and chewing tobacco compositions, is a tobacco free composition. That is, the tobacco substitute of the present invention possesses flavor, taste, appearance and aroma, as well as other desirable characteristics of snuff and chewing tobacco compositions, but do not contain nicotine or other hazardous products present in such tobacco containing products. Thus, the tobacco substitute of the present invention is especially efficacious as a bridging agent for those who have a desire to abstain from tobacco usage and who are so addicted to tobacco that ceasing usage is difficult.

The tobacco substitute of the present invention comprises a saliva permeable infusion pouch enveloping and sealingly retaining a casing solution wetted granular material. The infusion pouch is sized such that, when filled with the granulated material, the filled infusion pouch can be placed in a person's mouth adjacent the outer gum so as to function as a substitute for the use of tobacco and tobacco containing products. Further, as will be more clearly set forth hereafter, when using the tobacco substitute of the present invention no spittle discharge is necessary. Thus, the tobacco substitute serves as silent and undetectable mouth flavoring and breath refreshing lozenges, while at the same time providing a bridging substitute for abstaining from tobacco usage.

The use of the granulated material wetted with the casing solution and enveloped by the saliva permeable infusion pouch is believed important in order to provide the desired leaching efficacy of saliva thereon and thus to impart the desired taste effects from the tobacco substitute composition. Further, because the casing wetted material is in granular form, the placement of the casing wetted material in the saliva permeable infusion pouch is more readily accomplished than if such material were fluffy or elongated fibers. In addition to the granulated form, the material wetted by the casing solution and employed to fill the infusion pouch should be flavorless in order to allow one to impart the desired flavor to the material without the need of overcoming an inherent or distinct flavor of the particulate material. Similarly, it is desirable that the granulated material be colorless so that the material can easily be colored to simulate a tobacco product or other product; and the granulated material must be absorbent so that the material can be wetted by the casing solution and thereby maintain a moist condition throughout a normal shelf life of the tobacco substitute.

While any material satisfying the above stated requirements can be employed as the granulated material in the tobacco substitute of the present invention, especially desirable results have been obtained wherein the material is granulated cellulose. Further, cellulose is widely used in many commercially available food products, such as high fiber breads, cereas and the like. Thus, cellulose as an ingredient of the tobacco substitute would be readily acceptable by the purchasing public.

As previously stated, the tobacco substitute comprises a saliva permeable infusion pouch enveloping and sealingly retaining the casing wetted or moistened granulated cellulose therein. The particle size of the granulated cellulose can vary widely, the only requirement being that the particle size be sufficient so that a majority of the granulated cellulose is retained within the saliva permeable infusion pouch when placed in a person's mouth. However, the smaller the particle size of the granulated cellulose the greater will be the leaching efficacy of saliva thereon so as to impart the most intermediate, but shorter duration of taste effects therefrom; while a larger particle size of the granulated cellulose can impart greater longevity to the taste enjoyment of the user. Thus, while the amount of fines included in the granulated cellulose should be limited to that which is a tolerable passage percentage through the saliva permeable infusion pouch (discussed hereinbelow) so as to not offensive to user, a sufficient amount of fines should be included so as to provide nearly instantaneous taste awareness to the user. The amount of fines desired in the granulated cellulose can readily be determined experimentally so that the tobacco substitute will suit the taste selection of users. In a market sense, this affords the marketer means to provide a range of trade products much as is now available for tobacco products and for which the present invention directs itself as a substitute.

The granulated cellulose is wetted with a casing solution in order to impart the desired aroma, taste and color to the granulated cellulose and thereby satisfy the taste of the user of the tobacco substitute. Casing solutions are commonly used in the processing of tobacco products in order to enhance the aroma, flavor, and taste of the tobacco. Thus, casing solutions are well known in the tobacco art; and the casing solution constituent of the tobacco substitute of the present invention is employed to wet the granulated cellulose in a manner similar to which casing solutions are utilized in the processing of tobacco products.

The casing solution employed to wet the granulated cellulose is an aqueous solution containing varying amounts of flavoring agents, sweeteners, humectants and the like for imparting the desired taste and aroma characteristics to the granulated cellulose. The amount of each of the constituents employed in the aqueous casing solution, as well as the nature of the constituents, can vary widely. However, desirable results have been obtained wherein the casing solution employed to wet, and thus moisturize, the granulated cellulose contains from about 63 to about 82 weight percent water, from about 1 to about 5 weight percent of a flavoring agent, from about 15 to about 25 weight percent sweeteners and from about 2 to about 7 weight percent of a humectant. In addition, the aqueous casing solution can contain from about 0.05 to about 0.15 weight percent of a preservative to enhance the shelf life of the tobacco substitute and, a minor effective amount of a coloring agent for imparting a desired color to the granulated cellulose and the saliva permeable infusion pouch.

Any suitable flavoring agent which is compatible with a user's taste can be employed as the flavoring constituent in the aqueous casing solution. Typical of such flavoring agents are mint, wintergreen, lemon, cinnamon, strawberry and the like. As can be appreciated, other flavoring agents can be employed such as the flavoring agents customarily used in casing solutions for tobacco so that the tobacco substitute is provided with similar taste and aroma characteristics as the tobacco products for which it serves as a replacement.

Any suitable sweetener which is compatible with a user's taste can be employed in the formulation of the aqueous casing solution. Such sweeteners are well known in the casing art, and include sorbitol, sucrose, artificial sweeteners, mixtures thereof and the like.

In addition to the water, flavoring agent and sweeteners, the aqueous casing solutions generally contain from about 2 to about 7 weight percent of a humectant and from about 0.05 to about 0.15 weight percent of a preservative, based on the total weight of the aqueous casing solution. Any suitable humectant conventially used in the formulation of casing solutions for processing tobacco can be employed as the humectant in the aqueous casing solution for wetting the granulated cellulose of the tobacco substitute of the present invention. An example of such a humectant is glycerine. Similarly, any suitable preservative conventially used in casing solutions for processing tobacco can be employed as the preservative in the aqueous casing solution for wetting the granulated cellulose of the tobacco substitute, an example of such a preservative being potassium sorbate.

Because granulated cellulose has a high afinity for aqueous solutions, when it is determined desirable to color the particulate cellulose to simulate a tobacco product, or any other product, an effective minor amount of a water soluble food coloring agent can be incorporated in the aqueous casing solution. Food coloring agents are well known in the art, and thus no further comments concerning same are believed necessary to enable one to understand and appreciate the addition of the coloring agent to the aqueous casing solution. The only requirement in the selection of the coloring agent is that it have sufficient pigment to provide the casing solution with a desired color so that the granulated cellulose wetted with the casing solution will be colored to the desired color for which the product is to be marketed.

Figure 2:
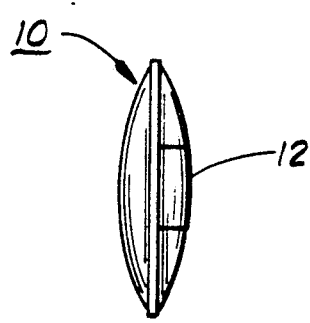
FIG. 2 is an end view of the infusion pouch of FIG. 1.

In manufacturing the tobacco substitute of the present invention the granulated cellulose having a selected mesh rating for satisfying the requirements discussed hereinbefore is selected and placed in a saliva permeable infusion pouch, such as depicted in FIGS. 1 and 2 and designated by the numeral 10. The infusion pouch 10 is an elongated member having a central portion 12 and sealed ends 14. The infusion pouch 10 if fabricated of an infusional filter paper packaging material capable of heat sealing. The infusion pouch 10 may be made by folding the granulated cellulose into the infusional filtering paper packaging material and heat sealing the seams, including the ends 14 thereof.

The dimension of the infusion pouch 10 can vary widely, but generally it is preferable that the length and height of the center portion 12 be about one inch and one-half inch, respectively. By fabricating the infusion pouch 10 with the before stated dimensions, the granulated cellulose filled infusion pouch can be comfortably placed in a person's mouth so as to be disposed between the outer gum and inner cheek. That is, since the infusion pouch 10 is to be disposed in a position for snuff-like ingestion via salivatory excretion of the person using same, the infusion pouch 10 is constructed to be saliva permeable while being comfortable to the user. In fact, once inserted into the mouth in the position stated, the user will soon be unaware of its presence except to enjoy the taste benefits thereof.

The technology for making saliva permeable infusion pouches is well known in the art and a further description of the fabrication of the infusion pouch 10 is not believed necessary to enable those skilled in the art to appreciate this present invention. For example, tobacco pouches are employed in the manufacture of smokeless tobacco marketed under the trademark BANDIT by U.S. Tobacco Company of Franklandpark, Ill.

In preparing the tobacco substitutes of the present invention the saliva permeable infusion pouch is filled with a predetermined amount of granulated cellulose having the desired particle size; and thereafter the cellulose filled saliva permeable infusion pouch is sealed by any suitable means, such as heat sealing so that the infusion pouch envelops and sealingly retains the granulated cellulose therein. The sealed, cellulose filled saliva permeable infusion pouch is then contacted with a sufficient amount of the aqueous casing composition for a period of time effective to thoroughly wet and thus moisten the granulated cellulose with the aqueous casing composition.

Any suitable means can be employed for contacting the cellulose filled infusion pouch with the aqueous casing solution, such as by spraying the aqueous casing solution onto the sealed pouch, dipping the cellulose filled pouch into the aqueous casing solution and the like.

Because of its absorbent characteristics, granulated cellulose will generally absorb up to about nine times its weight of the aqueous casing solution. In order to impart the desired moisture content to the granulated cellulose (and thus the tobacco substitute) it is generally desirable that the aqueous casing solution be present in the tobacco substitute in an amount of up to above thirty weight percent, based on the weight of the particulate cellulose, and more desirably from about 10 to about 20 weight percent, in order to insure that the texture of the casing moistened granulated cellulose is substantially comparable to the texture of tobacco. Thus, it may be necessary to remove excess casing solution from the cellulose filled pouch in order to provide the tobacco substitute with a desired moisture content to enhance its marketability.

Any suitable method can be employed for removing the excess aqueous casing solution from the cellulose filled pouch moistened with the aqueous casing solution. For example, excess casing solution can be controllably removed so that the casing solution is present in the granulated cellulose in the before described amounts by passing the tobacco substitute through a series of pinch rollers, by heating the tobacco substitute under controlled conditions to evaporate an excess aqueous casing solution, and the like. Such methods of controllably reducing moisture content of products, including tobacco products, is well known. Thus, no further description of the process for removing excess aqueous casing solution from the tobacco substitute of the present invention is believed necessary.

In order to further illustrate the present invention the following example is given. However, it is to be understood that the example is for illustrative purposes only and is not to be construed as limiting the scope of the subject invention.

EXAMPLE

A tobacco substitute capable of placement in a person's mouth adjacent the outer gum was produced as follows. A plurality of saliva permeable infusion pouches were fabricated of an infusable filter paper packaging material and each infusion pouch was filled with granulated cellulose. The granulated cellulose had a particle size which contained a minority of fines that could pass through the infusion pouch when wetted. Thus, the majority of the granulated cellulose was retained in the infusion pouches once the infusion pouches were sealed. The size of the infusion pouches was approximately one and one-half inches in length and one-half inch in height so that when filled with the granulated cellulose the cellulose filled infusion pouch could be readily placed adjacent a person's outer gum without distorting the person's mouth or making the person uncomfortable.

The cellulose filled infusion pouches were then contacted with a casing solution so as to wet the granulated cellulose. The casing solution was formulated by admixing the following ingredients.

| INGREDIENTS | PERCENTAGE (WEIGHT) |
| --- | --- |
| Water | 71.0 |
| Flavoring* | 4 |
| Sorbitol Powder | 19.3 |
| Glycerine | 5 |
| Artificial Sweetener (aspartane) | 0.6 |

| INGREDIENTS | PERCENTAGE (WEIGHT) |
| --- | --- |
| Potassium Sorbate | 0.1 |

The granulated cellulose sealed with the infusion pouches absorbed approximately nine times its weight of the casing solution.

In order to reduce the amount of casing solution in the granulated cellulose, and to provide a tobacco substitute having a casing content of less than 30 weight percent, the casing wetted cellulose filled infusion pouches were squeezed to remove excess casing solution. The resulting tobacco substitutes had a moist feeling similar to that of conventional tobacco products packaged in saliva permeable infusion pouches and, when placed adjacent the outer gum, provided the user with a pleasant taste which substituted for the use of tobacco.

Several different flavoring agents were employed to flavor the casing solution described above. Examples of such flavoring agents employed are lemon extract, mint, wintergreen, and cinnamon.

As will be understood, certain of the flavoring agents impart a characteristic color to both the granulated cellulose and the saliva permeable infusion pouch. However, should one desire to alter the color of the tobacco substitute, one needs to merely add a minor effective amount of a suitable water soluble coloring agent.

The tobacco substitute, when placed in one's mouth in area adjacent an outer gum assists in reducing one's dependency on tobacco. Further, because of the porous nature of the saliva permeable infusion pack, saliva induced juices contained within the pouch can readily be dispersed into the user's mouth and digestive system without the need for spittle of such juices. However, it should be understood that the tobacco substitute is not a substitute for chewing tobacco as a chewing action on the pouch would rupture the pouch and a discharge the pouch's ingredients into either the person's mouth or gum area.

It is clear that the present invention is well adapted to carry out the objects and to obtain the ends and advantages mentioned as well as those inherent therein. While a presently preferred embodiment has been described for the purpose of this disclosure, numerous changes may be made which will readily suggest themselves to those skilled in the art and which are encompassed within the spirit of the invention disclosed and as defined in the appended claims.

What is claimed is:

1. A method for producing an improved tobacco substitute in a saliva permeable infusion pouch comprising:
    filling the saliva permeable infusion pouch with granulated cellulose, the cellulose filled saliva permeable infusion pouch sized to be positioned in a person's mouth in an area adjacent the outer gum;
    sealing the cellulose filled saliva permeable infusion pouch; and
    contacting the sealed, cellulose filled saliva permeable infusion pouch with an aqueous casing solution for a period of time effective to moisten the granulated cellulose with the aqueous casing solution, the aqueous casing solution consisting essentially of from about 63 to about 82 weight percent water, from about 1 to about 5 weight percent of a flavoring agent, from about 15 to about 25 weight percent sweetener and from about 2 to about 7 weight percent of a humectant.

2. The method of claim 1 wherein the aqueous casing solution further contains an effective minor amount of a coloring agent for imparting a preselected color to the aqueous casing solution moistened granular cellulose.

3. The method of claim 1 wherein the aqueous casing solution further contains from about 0.05 to about 0.15 weight percent of a preservative.

4. The method of claim 3 wherein the aqueous casing solution contains about 71 weight percent water, about 4 weight percent of a flavoring agent, about 5 weight percent of a humectant wherein the humectant is glycerine, about 19.9 weight percent of sweeteners and about 0.1 weight percent of a preservative wherein the preservative is potassium sorbate.

5. The method of claim 1 further comprising removing excess aqueous casing solution from the moistened cellulose filled saliva permeable infusion pouch to provide an improved tobacco substitute containing from about 10 to about 20 weight percent of the aqueous casing solution.

6. A tobacco substitute positionable in a person's mouth adjacent the outer gum, the tobacco substitute comprising:
    granulated cellulose;
    an effective amount of a casing solution sufficient to maintain the granulated cellulose in a moist condition, the effective amount of the casing solution being an amount sufficient to provide up about 30 weight percent of the casing solution in the tobacco substitute based on the weight of the granulated cellulose; and
    a saliva permeable infusion pouch enveloping and sealingly retaining the casing solution moistened cellulose, the saliva permeable infusion pouch fabricated of an infusional filter paper packaging material.

7. The tobacco substitute of claim 6 wherein the amount of the casing solution employed to moisten the granulated cellulose is an amount sufficient to provide rom about 10 to about 20 weight percent of the casing solution, based on the weight of the granulated cellulose.

8. The tobacco substitute of claim 6 wherein the casing solution consists essentially of from about 63 to about 82 weight percent water, from about 1 to about 5 weight percent of a flavoring agent, from about 15 to about 25 weight percent of a sweetener and from about 2 to about 7 weight percent of a humectant.

9. The tobacco substitute of claim 8 wherein the aqueous casing solution further contains from about 0.05 to about 0.15 weight percent of a preservative.

10. The tobacco substitute of claim 9 wherein the aqueous casing solution further contains an effective minor amount of a coloring agent for imparting a preselected color to the aqueous casing solution moistened granular cellulose.

11. The tobacco substitute of claim 10 wherein the aqueous casing solution contains about 71 weight percent water, about 4 weight percent of a flavoring agent selected from the group consisting of mint, cinnamon, lemon, wintergreen and strawberry, about 5 weight percent of a humectant wherein the humectant is glycerine, about 19.9 weight percent sweeteners and about 0.1 weight percent of a preservative wherein the preservative is potassium sorbate.

12. A method for reducing dependency on tobacco comprising placing in one's mouth in an area adjacent an outer gum, a saliva permeable infusion pouch filled with granulated cellulose moistened with up to about 30 weight percent, based on the weight of the granulated cellulose, of a casing solution consisting essentially of from about 63 to about 82 weight percent water, from about 1 to about 5 weight percent of a flavoring agent, from about 15 to about 25 weight percent sweetener and from about 2 to about 7 weight percent of a humectant.

13. The method for reducing dependency on tobacco of claim 12 wherein the filled saliva permeable infusion pouch is maintained in the mouth during periods of craving for tobacco.

14. The method for reducing dependency on tobacco of claim 13 wherein the saliva permeable infusion pouch sealingly retains the casing solution moistened granulated cellulose, and wherein the saliva permeable infusion pouch is fabricated of an infusional filter paper packaging material.

15. The method for reducing dependency on tobacco of claim 14 wherein the casing solution further contains an effective minor amount of a coloring agent for imparting a preselected color to the casing solution moistened granulated cellulose.

16. The method for reducing dependency on tobacco of claim 14 wherein the casing solution further comprises from about 0.05 to 0.15 weight percent of a preservative.

17. The method for reducing dependency on tobacco of claim 14 wherein the amount of the casing solution employed to moisten the granulated cellulose is an amount sufficient to provide from about 10 to about 20 weight percent of the casing solution based on the weight of the granulated cellulose.

* * * * *

UNITED STATES PATENT AND TRADEMARK OFFICE
CERTIFICATE OF CORRECTION

PATENT NO. : 5,167,244
DATED : December 1, 1992
INVENTOR(S) : Randy Eugene Kjerstad It is certified that error appears in the above-indentified patent and that said Letters Patent is hereby corrected as shown below:

Cover Page, (54), Title: after "TOBACCO SUBSTITUTE" insert --AND METHOD FOR PRODUCING AND USING SAME--;

Cover Page, (56), References Cited:
after "2,930,720  3/1960   Finberg" insert --131/17--;
after "3,067,068  12/1962  Finberg" insert --131/2--;
after "3,071,476  1/1963   Werft et al." insert --99/135--;
after "3,369,551  2/1968   Carroll" insert --131/2--
after "3,757,798  9/1973   Lambert" insert --131/1--; and
after "4,431,680  2/1984   Yoshida" insert --426/538--.

Column 1, line 1, after "TOBACCO SUBSTITUTE" insert --AND METHOD FOR PRODUCING AND USING SAME--;

Column 3, line 41, delete "cereas" and substitute therefor --cereals--; and

Column 8, line 44, delete "rom" and substitute therefor --from--.

Signed and Sealed this

Twenty-sixth Day of April, 1994

Attest:

BRUCE LEHMAN

*Attesting Officer*  *Commissioner of Patents and Trademarks*